(12) United States Patent  (10) Patent No.: US 7,531,571 B2
Veeneman et al.  (45) Date of Patent: *May 12, 2009

(54) CHROMAN DERIVATIVES AS ESTROGENIC COMPOUNDS

(75) Inventors: Gerrit Herman Veeneman, Schaijk (NL); Neeltje Miranda Teerhuis, Wijchen (NL)

(73) Assignee: N.V. Organon, Oss (NL)

( * ) Notice: Subject to any disclaimer, the term of this patent is extended or adjusted under 35 U.S.C. 154(b) by 212 days.

This patent is subject to a terminal disclaimer.

(21) Appl. No.: 11/328,760

(22) Filed: Jan. 10, 2006

(65) Prior Publication Data

US 2006/0160889 A1 Jul. 20, 2006

Related U.S. Application Data

(63) Continuation of application No. 10/220,509, filed as application No. PCT/EP01/02144 on Feb. 26, 2001, now Pat. No. 7,214,706.

(30) Foreign Application Priority Data

Mar. 1, 2000 (EP) .................................. 00200713

(51) Int. Cl.
 A61K 31/35 (2006.01)
 C07D 407/00 (2006.01)
(52) U.S. Cl. ...................... 514/457; 549/399
(58) Field of Classification Search ................. 549/399; 514/457
 See application file for complete search history.

(56) References Cited

U.S. PATENT DOCUMENTS

| 3,340,276 | A | 9/1967 | James et al. | 260/345.2 |
| 3,535,344 | A | 10/1970 | Irmscher et al. | 260/345.2 |
| 5,952,364 | A | 9/1999 | Bryant et al. | 514/408 |

FOREIGN PATENT DOCUMENTS

| DE | 1543749 | 12/1969 |
| EP | 0798378 A2 | 10/1997 |
| WO | WO 94/20098 | 9/1994 |
| WO | WO 96/21444 | 7/1996 |
| WO | WO 98/18771 | 5/1998 |

OTHER PUBLICATIONS

International Search Report, No. PCT/EP01/02144, Jul. 11, 2001.
Mosselman et al., "ERβ: identification and characterization of a novel human estrogen receptor," FEBS Letters 392; pp. 49-53 (1996).
Hestiantoro et al., "Changes in Estrogen Receptor-α and -β in the Infundibular Nucleus of the Human Hypothalamus Are Related to the Occurrence of Alzheimer's Disease Neuropathology," Journal of Clinical Enhocrinology & Metabolism, 89(4) pp. 1912-1925 (2004).
Nilsson et al., "ERβ: a Novel Estrogen Receptor Offers the Potential for New Drug Development," TEM vol. 9, No. 10, pp. 387-395 (1998).

*Primary Examiner*—Janet L. Andres
*Assistant Examiner*—Raymond Covington
(74) *Attorney, Agent, or Firm*—Susan Hess

(57) ABSTRACT

The invention provides chroman compounds having formula 1

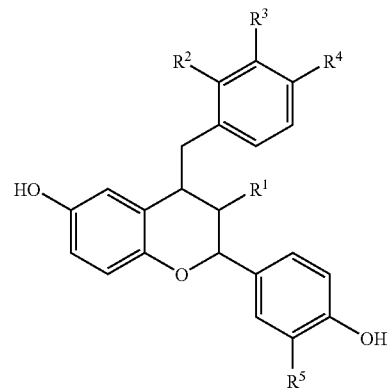

Formula 1 wherein $R^1$ is (1C-4C)alkyl, (2C-4C)alkenyl or (2C-4C)alkynyl, and independently $R^1$ has a cis-orientation in relation to the exocyclic phenyl group at the 2-position of the skeleton; $R^4$ is H, Hal, $CF_3$, OH or (1C-2C)alkyloxy; $R^2$, $R^3$, and $R^5$ are independently H, Hal, $CF_3$, (1C-4C)alkyl, (2C-4C)alkenyl or (2C-4C)alkynyl and prodrugs thereof for the manufacture of a medicine for estrogen-receptor related treatments.

5 Claims, No Drawings

CHROMAN DERIVATIVES AS ESTROGENIC COMPOUNDS

This application is a continuation of U.S. application Ser. No. 10/220,509, filed Aug. 30, 2002 now U.S. Pat. No. 7,214,706 which claims priority based on PCT Application No.: PCT/EP01/02144, filed Feb. 26, 2001, which claims priority on European Patent Application No. 00200713.6, filed Mar. 1, 2000.

FIELD OF THE INVENTION

The present invention relates to chroman compounds having affinity for estrogen receptors and to the use of such a compound for the manufacture of a medicine for use in estrogen-receptor related treatments.

BACKGROUND OF THE INVENTION

Compounds with a 4-phenylchroman skeleton and a phenyl ring at the 3 position with particular emphasis on the nature of the cis-trans configuration of the substituents at the 3 and 4 position (locants are according to the rules of Chemical Abstracts) are described in WO 98/18771 for estrogenic therapies. Although there is a keen interest in compounds with affinity for the estrogen receptor, new compounds with a 4-benzyl-2-phenylchroman skeleton and affinity for the estrogen receptor cannot be learnt from this document.

The interest in new compounds with affinity for the estrogen receptor stems from unsatisfactory results with known estrogenic compounds for osteoporosis treatment and treatment of other postmenopausal complaints and from the discovery of two distinct types of receptors, denoted ERα and ERβ (see Mosselman et al., *FEBS Letters* 392 (1996) 49-53 as well as EP-A-0 798 378). Since these receptors have a different distribution in human tissue, the finding of compounds which possess a selective affinity for either of the two is an important technical progress, making it possible to provide a more selective treatment in estrogen-receptor related medical treatments, such as those for contraception and for treatment of menopausal complaints, osteoporosis, and estrogen dependent tumour control, with a lower burden of estrogen-related side-effects.

BRIEF SUMMARY OF THE INVENTION

The present invention is based on the finding that compounds with a 4-benzyl-2-phenylchroman skeleton with hydroxyl substitutions at specific locations, possess surprisingly high estrogen receptor affinity. Moreover, the present invention pertains to such compounds as compound with selective affinity for the estrogen β-receptors (ERβ).

DETAILED DESCRIPTION OF THE INVENTION

More specifically, the invention provides a chroman compound, or a prodrug thereof, having formula 1

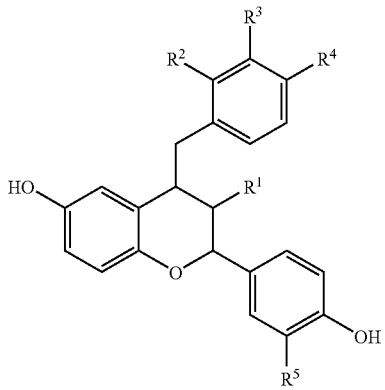

Formula 1 in which

R$^1$ is (1C-4C)alkyl, (2C-4C)alkenyl or (2C-4C)alkynyl, and independently R$^1$ has a cis-orientation in relation to the exocyclic phenyl group at the 2-position of the skeleton;

R$^4$ is H, Hal, CF$_3$, OH or (1C-2C)alkyloxy;

R$^2$, R$^3$, and R$^5$ are independently H, Hal, CF$_3$, (1C-4C)alkyl, (2C-4C)alkenyl or (2C-4C)alkynyl.

More preferred compounds which are more effective and the more selective agonists for the ERβ-estrogen receptors are compounds having formula 1, wherein R$^1$ is (1C-4C) alkyl, whereby R$^1$, the exocyclic phenyl group at the 2-position and the exocyclic substituent at the 4-position of the chroman skeleton all have a cis-orientation; R$^2$ is H, F or Cl; R$^3$ and R$^4$ are H; R$^5$ is H or CH$_3$.

Most preferred compounds are compounds having formula 1, wherein R$^1$ is methyl or ethyl in cis-orientation with the exocyclic phenyl group at the 2-position and the exocyclic substituent at the 4-position of the chroman skeleton; R$^2$ is H or F; R$^3$, R$^4$ and R$^5$ are H.

A prodrug is defined as being a compound which converts in the body of a recipient to a compound as defined by the formula 1. Notably, the hydroxy groups at the 6 position and the 4-phenyl position of the skeletons of formula a can for example be substituted by alkyl*oxy, alkenyl*oxy, acyl*oxy, aroyloxy, alk*oxycarbonyloxy, sulfonyl groups or phosphate groups, whereby the carbon chain length of the groups denoted with an asterisk (*) is not considered to be sharply delimited, while aroyl generally will comprise a phenyl, pyridinyl or pyrimidyl, which groups can have substitutions customary in the art, such as alkyl*oxy, hydroxy, halogen, nitro, cyano, and (mono-, or dialkyl*-)amino. The length of the alkyl, alkenyl and acyl groups is selected depending on the desired properties of the prodrugs, whereby the longer chained prodrugs with for example lauryl or caproyl chains are more suitable for sustained release and depot preparations. It is known that such substituents spontaneously hydrolyse or are enzymatically hydrolysed to the free hydroxyl substituents on the skeleton of the compound. Such prodrugs will have biological activity comparable to the compounds to which they are converted in the body of the recipients. The active compound to which a prodrug is converted is called the parent compound. The onset of action and duration of action as well as the distribution in the body of a prodrug may differ from such properties of the parent compound. For other types of prodrugs it should be realised that the hydroxyl groups in compounds according to the formula 1 can be placed in position by the metabolic system of the recipient.

The hydroxyl groups are essential for affinity for the estrogen receptors. Thus, compounds as defined by the formula 1, but lacking one or both hydroxyl groups are also made available as compounds according to this invention, and to which compounds is referred as prodrugs.

Other terms used in this description have the following meaning:

alkyl is a branched or unbranched alkyl group, for example methyl, ethyl, propyl, isopropyl, butyl, sec-butyl, tert-butyl, hexyl, octyl, capryl, or lauryl;

alkenyl is a branched or unbranched alkenyl group, such as ethenyl, 2-butenyl, etc.;

alkynyl is a branched or unbranched alkynyl group, such as ethynyl and propynyl;

aryl is a monocyclic or heterocyclic aromatic ring system;

aroyl is arylcarbonyl such as a benzoyl group;

alkanoyl is an 1-oxoalkyl group acyl is an alkanoyl or aroyl group;

Hal and halogen refers to fluorine, chlorine, bromine and iodine

The prefixes (1C-4C), (2C-4C) etc. have the usual meaning to restrict the meaning of the indicated group to those with 1 to 4, 2 to 4 etc. carbon atoms.

The compounds of this invention contain at least three centres of chirality and can exist as enantiomers and diastereomers. The present invention includes the aforementioned enantiomers and diastereomers within its scope and each of the individual (R) and (S) enantiomers and their salts, substantially free, i.e. associated with less than 5%, preferably less than 2%, in particular less than 1% of the other enantiomer and mixtures of such enantiomers in any proportions including racemic mixtures containing substantially equal amounts of the two enantiomers.

It should be realised that substitution variants can be made of the compounds of the present invention, without need to go beyond the present invention. A substitution variant is defined as being a compound which comprises in its molecular structure the structure as defined by formula 1. The skilled person inspecting the group of compounds defined by these formulas will immediately understand that modification by a substituent to the skeleton can yield a compound with similar biological activity as the compound without this particular substituent. It is common practice in the art to test such substitution variants for the expected biological activity so that it is a routine skill to obtain useful substitution variants of compounds as defined by formula 1.

The estrogen-receptor affinity profile of the compounds according to the present invention, makes them suitable as improved estrogens, in the sense that they can be used for estrogen-receptor related medical treatments, such as those for contraception or for treatment or prevention of benign prostate hypertrophy, cardiovascular disorders, menopausal complaints, osteoporosis, estrogen dependent tumour control or central nervous system disorders such as depression or Alzheimer's disease. The preferred compounds of the invention, which have the more selective affinity for the ERβ receptor, are particularly suitable for estrogen-receptor related medical treatments under diminished estrogen-related side-effects. This is most desirable when these compounds are used in the treatment of osteoporosis, cardiovascular disorders, prostate disorders and central nervous system disorders such as depression or Alzheimer's disease.

The compounds of the invention can be produced by various methods known in the art of organic chemistry in general.

More specifically the routes of synthesis as illustrated in the schemes of the examples can be used.

4-Benzyl chromanes can be prepared as DL mixtures from reaction of the appropriate chromenylium salts with a substituted or nonsubstituted benzylmagnesium chloride, followed by hydrogenation of the resulting 2,3-chromenes (see Scheme 1, in which $R^6$ and $R^7$ are protecting groups, such as benzyls or methyl, as are commonly known in the art, and the group R represents a benzyl group optionally substituted with $R^2$, $R^3$ and/or $R^4$).

The chromenylium salts can be derived from reaction of 5-benzyloxy, 5-methoxy or 5-hydroxy-2-hydroxy-benzaldehyde and an appropriate alkyl-phenylketone in the presence of trifluoromethanesulphonic acid. The alkyl-phenylketones are either commercially available or can be prepared according to the method performed in example 1.

Scheme 1. Preparation of 4-benzyl-chromanes

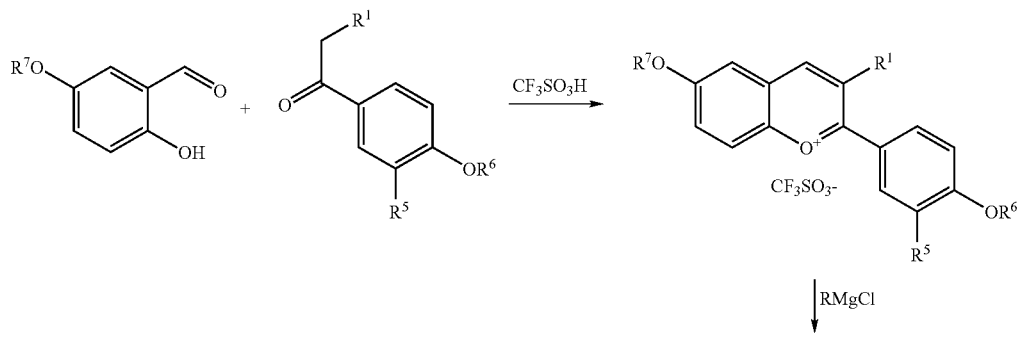

-continued

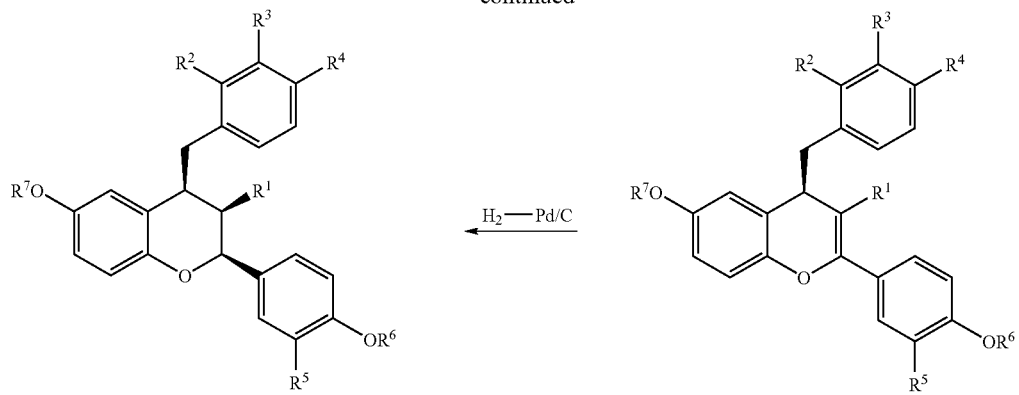

Ester prodrugs can be made by esterification of compounds with free hydroxyl groups by reaction with appropriate acyl chlorides in pyridine.

The present invention also relates to a pharmaceutical composition comprising a chroman compound according to the invention mixed with a pharmaceutically acceptable auxiliary, such as described in the standard reference Gennaro et al., *Remmington's Pharmaceutical Sciences*, (18th ed., Mack publishing Company, 1990, see especially Part 8: Pharmaceutical Preparations and Their Manufacture). The mixture of the compounds according to the invention and the pharmaceutically acceptable auxiliary may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. nasal spray. For making dosage units, e.g. tablets, the use of conventional additives such as fillers, colorants, polymeric binders and the like is contemplated. In general any pharmaceutically acceptable additive which does not interfere with the function of the active compounds can be used. The compounds of the invention may also be included in an implant, a vaginal ring, a patch, a gel, and any other preparation for sustained release.

Suitable carriers with which the compositions can be administered include lactose, starch, cellulose derivatives and the like, or mixtures thereof used in suitable amounts.

Furthermore, the invention relates to the use of a chroman compound according to the invention for the manufacture of a medicament for estrogen-receptor related treatments, in particular for treatment of estrogen-receptor related disorders such as peri- and/or post-menopausal complaints. Thus the invention also pertains to the medical indications of peri- and/or post-menopausal (climacteric) complaints and osteoporosis, i.e. a method of treatment in the field of hormone replacement therapy (HRT), comprising the administration to a patient, being a woman, of a compound as described herein before (in a suitable pharmaceutical dosage form).

Further, the invention relates to the use of a chroman compound according to the invention in the manufacture of a medicament having contraceptive activity. Thus the invention also pertains to the medical indication of contraception, i.e. a method of contraception comprising the administration to a subject, being a woman or a female animal, of a progestogen and an estrogen as is customary in the field, wherein the estrogen is a compound as described herein before (in a suitable pharmaceutical dosage form).

Finally the invention relates to the use of a chroman compound according to the invention for the manufacture of a medicament having selective estrogenic activity, such a medicament being generally suitable in the area of HRT.

The dosage amounts of the present compounds will be of the normal order for estradiol derivatives, e.g. of the order of 0.01 to 10 mg per administration.

The invention is further illustrated hereinafter with reference to some unlimitative examples and the corresponding formula schemes referred to.

EXAMPLES

In the examples the compounds are identified with numbers, for example 1a, 1b, 2b etc. These numbers refer to the definitions of the compounds in the schemes. In the schemes the following abbreviations are used: Bn=benzyl, Et=ethyl, Me=methyl, Pr=propyl, Piv=pivaloyl.

Example 1

General Procedure for the Preparation of a 4-Hydroxy-1-acyl-benzene

The appropriate phenol was dissolved in dichloromethane (3 ml/mmol). The solution was cooled in an ice-bath under a nitrogen atmosphere. To this solution anhydrous aluminium chloride (2 eq) was added in small portions. Then a solution of an (1C-4C)alkanyol chloride (1 eq) in dichloromethane (1 ml/mmol) was added dropwise. The reaction mixture was stirred overnight (approx. 18 hours) at ambient temperature.

The reaction mixture was carefully poured into ice-water. The precipitated product was extracted with ethyl acetate. The organic layer was extracted twice with 2N sodium hydroxide solution. The combined aqueous layers were washed twice with diethyl ether. The aqueous layer was acidified while stirring with concentrated hydrochloric acid to pH 5. The precipitated product was extracted with diethyl ether. The organic layer was dried over anhydrous magnesium sulphate and the solvent was evaporated. The 4-hydroxy-1-acyl-benzenes (e.g. compound 2f) were obtained in 30-70% yields.

General Procedure for the Preparation of a 4-Benzyloxy- or a 4-Methoxy-1-acyl-benzene (e.g. Compounds 2a-e):

Benzylation or methylation was achieved by reaction of the 4-hydroxy-1-acyl-benzenes with benzyl bromide (1.2 eq) or methyl iodide (4 eq) in acetone (5-10 ml/mmol) in the presence of potassium carbonate (2 eq).

The reaction mixture was refluxed for 1-3 hour. The reaction mixture was cooled to room temperature and ethyl acetate and water were added. The organic layer was washed once with 10 ml of 2N sodium hydroxide solution, dried on magnesium sulphate and concentrated

Example 2

Preparation of Chromenylium Salts 3 according to Scheme 2

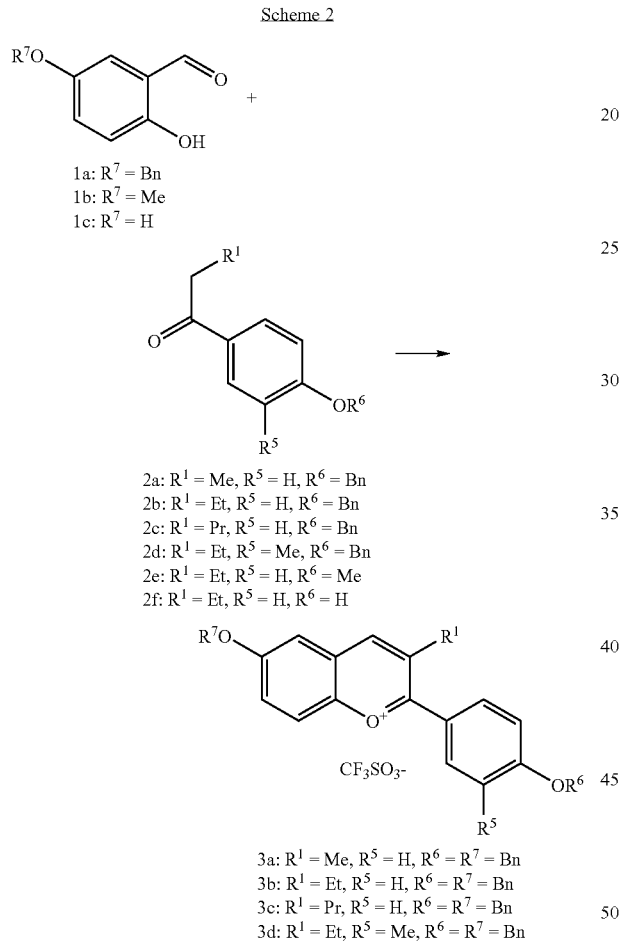

Scheme 2

1a: $R^7$ = Bn
1b: $R^7$ = Me
1c: $R^7$ = H

2a: $R^1$ = Me, $R^5$ = H, $R^6$ = Bn
2b: $R^1$ = Et, $R^5$ = H, $R^6$ = Bn
2c: $R^1$ = Pr, $R^5$ = H, $R^6$ = Bn
2d: $R^1$ = Et, $R^5$ = Me, $R^6$ = Bn
2e: $R^1$ = Et, $R^5$ = H, $R^6$ = Me
2f: $R^1$ = Et, $R^5$ = H, $R^6$ = H

3a: $R^1$ = Me, $R^5$ = H, $R^6$ = $R^7$ = Bn
3b: $R^1$ = Et, $R^5$ = H, $R^6$ = $R^7$ = Bn
3c: $R^1$ = Pr, $R^5$ = H, $R^6$ = $R^7$ = Bn
3d: $R^1$ = Et, $R^5$ = Me, $R^6$ = $R^7$ = Bn

One of a 5-benzyloxy- [T. Kappe et al., Arch. Pharmaz.; 308, 339-346 (1975)], 5-hydroxy-, or 5-methoxy-2-hydroxybenzaldehyde 1a-c (1 mmol) and one of an appropriate ketone 2a-f (1 mmol) were dissolved in 5 ml of diethyl ether. The solution was cooled in an ice-bath. Trifluoromethanesulfonic acid (2 mmol) was added dropwise and the reaction mixture was stirred overnight (approx. 18 hours) at ambient temperature.

The precipitated red/brown products 3a-d were collected by filtration, thoroughly washed with 20 ml of diethyl ether and dried in vacuo. The yields varied between 50-80%. (see table below).

| Product | Yield (% of theory) |
|---|---|
| 3a | 73 |
| 3b | 70 |
| 3c | 54 |
| 3d | 52 |

Example 3

Preparation of 4-Benzyl-chromanes 5a-5k According to Scheme 3

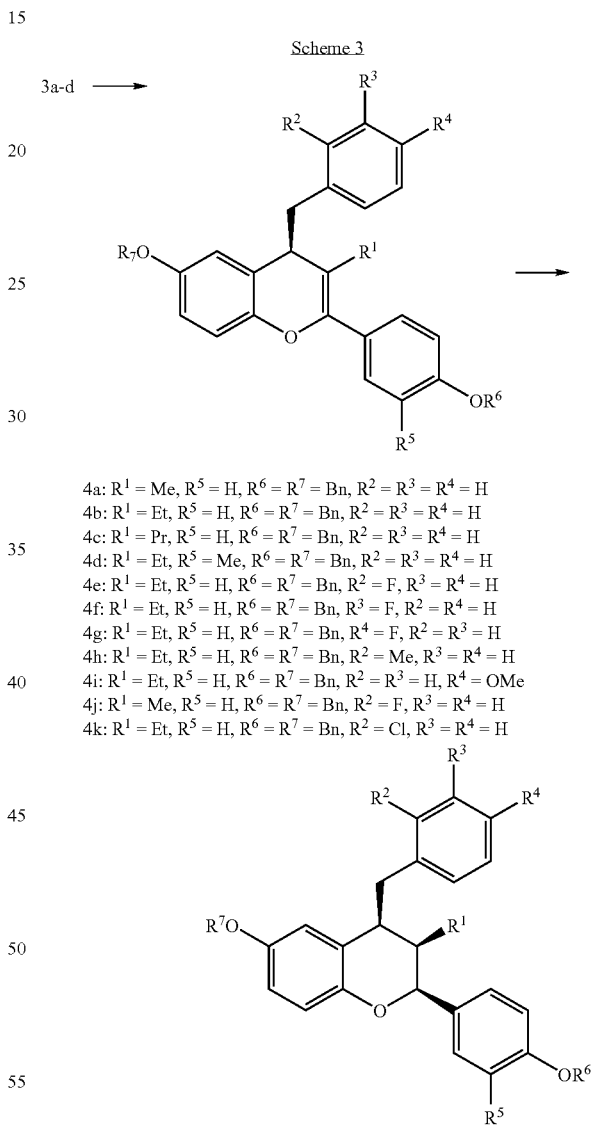

Scheme 3

3a-d →

4a: $R^1$ = Me, $R^5$ = H, $R^6$ = $R^7$ = Bn, $R^2$ = $R^3$ = $R^4$ = H
4b: $R^1$ = Et, $R^5$ = H, $R^6$ = $R^7$ = Bn, $R^2$ = $R^3$ = $R^4$ = H
4c: $R^1$ = Pr, $R^5$ = H, $R^6$ = $R^7$ = Bn, $R^2$ = $R^3$ = $R^4$ = H
4d: $R^1$ = Et, $R^5$ = Me, $R^6$ = $R^7$ = Bn, $R^2$ = $R^3$ = $R^4$ = H
4e: $R^1$ = Et, $R^5$ = H, $R^6$ = $R^7$ = Bn, $R^2$ = F, $R^3$ = $R^4$ = H
4f: $R^1$ = Et, $R^5$ = H, $R^6$ = $R^7$ = Bn, $R^3$ = F, $R^2$ = $R^4$ = H
4g: $R^1$ = Et, $R^5$ = H, $R^6$ = $R^7$ = Bn, $R^4$ = F, $R^2$ = $R^3$ = H
4h: $R^1$ = Et, $R^5$ = H, $R^6$ = $R^7$ = Bn, $R^2$ = Me, $R^3$ = $R^4$ = H
4i: $R^1$ = Et, $R^5$ = H, $R^6$ = $R^7$ = Bn, $R^2$ = $R^3$ = H, $R^4$ = OMe
4j: $R^1$ = Me, $R^5$ = H, $R^6$ = $R^7$ = Bn, $R^2$ = F, $R^3$ = $R^4$ = H
4k: $R^1$ = Et, $R^5$ = H, $R^6$ = $R^7$ = Bn, $R^2$ = Cl, $R^3$ = $R^4$ = H

5a: $R^1$ = Me, $R^5$ = H, $R^6$ = $R^7$ = H, $R^2$ = $R^3$ = $R^4$ = H
5b: $R^1$ = Et, $R^5$ = H, $R^6$ = $R^7$ = H, $R^2$ = $R^3$ = $R^4$ = H
5c: $R^1$ = Pr, $R^5$ = H, $R^6$ = $R^7$ = H, $R^2$ = $R^3$ = $R^4$ = H
5d: $R^1$ = Et, $R^5$ = Me, $R^6$ = $R^7$ = H, $R^2$ = $R^3$ = $R^4$ = H
5e: $R^1$ = Et, $R^5$ = H, $R^6$ = $R^7$ = H, $R^2$ = F, $R^3$ = $R^4$ = H
5f: $R^1$ = Et, $R^5$ = H, $R^6$ = $R^7$ = H, $R^3$ = F, $R^2$ = $R^4$ = H
5g: $R^1$ = Et, $R^5$ = H, $R^6$ = $R^7$ = H, $R^4$ = F, $R^2$ = $R^3$ = H
5h: $R^1$ = Et, $R^5$ = H, $R^6$ = $R^7$ = H, $R^2$ = Me, $R^3$ = $R^4$ = H
5i: $R^1$ = Et, $R^5$ = H, $R^6$ = $R^7$ = H, $R^2$ = $R^3$ = H, $R^4$ = OMe
5j: $R^1$ = Me, $R^5$ = H, $R^6$ = $R^7$ = H, $R^2$ = F, $R^3$ = $R^4$ = H
5k: $R^1$ = Et, $R^5$ = H, $R^6$ = $R^7$ = H, $R^2$ = Cl, $R^3$ = $R^4$ = H

General Procedure

The chromenylium salt 3a-d was suspended in 10 ml of dry diethyl ether (10 ml/mmol). The suspension was cooled in an Ethanol/$CO_2$-bath to −78° C. The appropriate benzylmagnesium chloride (2M solution in THF, 3 eq) was added with the use of a syringe. The solution was stirred for 0.5 hour at −78° C. The reaction mixture was diluted with saturated ammonium chloride solution and extracted with ethyl acetate. The organic layer was washed twice with water and once with saturated sodium chloride solution, dried over anhydrous magnesiumsulphate and the solvent was evaporated. The residue was purified by either recrystallization from ethanol or by column chromatography (heptane/ethyl acetate) to give pure 4a-k in 32-95% of the theoretical yield (see table below).

| Product | Yield (% of theory) | $R_f$-value |
|---|---|---|
| 4a | 87 | 0.65 (Toluene/diethyl ether 1:1) |
| 4b | 75 | 0.61 (Heptane/ethyl acetate 7:3) |
| 4c | 82 | 0.67 (Heptane/ethyl acetate 7:3) |
| 4d | 32 | 0.63 (Heptane/ethyl acetate 7:3) |
| 4e | 60 | 0.62 (Heptane/ethyl acetate 7:3) |
| 4f | 72 | 0.64 (Heptane/ethyl acetate 7:3) |
| 4g | 76 | 0.66 (Heptane/ethyl acetate 7:3) |
| 4h | 47 | 0.73 (Heptane/ethyl acetate 7:3) |
| 4i | 57 | 0.61 (Heptane/ethyl acetate 7:3) |
| 4j | 92 | 0.60 (Heptane/ethyl acetate 4:1) |
| 4k | 95 | 0.50 (Heptane/ethyl acetate 4:1) |

1 mmol of one of a substituted 4-benzyl-chroman 4a-k was dissolved in 35 ml of ethyl acetate. To this solution 1 mg of palladium on carbon (10% w/w) per 4 mg was added and hydrogen was passed through the reaction mixture for 2 hours while stirring. The catalyst was removed by filtration and washed with 10 ml of ethyl acetate and the filtrate was concentrated under reduced pressure.

The crude product was purified by column chromatography (toluene/diethyl ether or heptane/ethyl acetate) to give pure 5a-k in 35-98% of the theoretical yield (see tables below).

| Product | Yield (% of theory) | $R_f$-value |
|---|---|---|
| 5a | 56 | 0.52 (Toluene/diethyl ether 1:1) |
| 5c | 52 | 0.56 (Toluene/diethyl ether 1:1) |
| 5d | 47 | 0.48 (Toluene/diethyl ether 1:1) |
| 5f | 72 | 0.49 (Toluene/diethyl ether 1:1) |
| 5g | 76 | 0.39 (Toluene/diethyl ether 1:1) |
| 5h | 42 | 0.40 (Heptane/ethyl acetate 2:1) |
| 5i | 52 | 0.57 (Toluene/diethyl ether 1:1) |
| 5k | 64 | 0.60 (Heptane/ethyl acetate 2:1) |

| Product | Yield (% of theory) | $^1$H-NMR($\delta$, $CDCl_3$, 400MHz) |
|---|---|---|
| 5b | 98 | 7.37-6.63(12H), 5.21(s, 1H), 4.82(s, 1H), 4.51(s, 1H), 3.61(m, 1H), 3.40(dd, 1H), 2.75(dd, 1H), 1.74(m, 1H), 1.34(m, 1H), 1.16(m, 1H), 0.30(t, 3H). |
| 5e | 85 | 7.28-6.64(11H), 5.23(s, 1H), 4.82(s, 1H), 4.51(s, 1H), 3.65(m, 1H), 3.38(dd, 1H), 2.81(dd, 1H), 1.70(m, 1H), 1.35(m, 1H), 1.18(m, 1H), 0.28(t, 3H). |
| 5j | 35 | 7.31-6.66(11H), 5.11(s, 1H), 4.85(s, 1H), 4.56(s, 1H), 3.69(m, 1H), 3.45(dd, 1H), 2.72(dd, 1H), 1.84(m, 1H), 0.66(d, 3H). |

Example 4

Separation of the Enantiomers of Chroman 5k

The enantiomers were separated using a chiral HPLC-column (Chiralpak AD) with hexane/ethanol as eluent.

(+)-enantiomer (optical purity>95%): $[\alpha]_D$+10.4 (c=0.5, dioxane)

(−)-enantiomer (optical purity>95%): $[\alpha]_D$−10.8 (c=0.5, dioxane)

Example 5

Preparation of Acyl Esters 6a and 6b

Formula 2

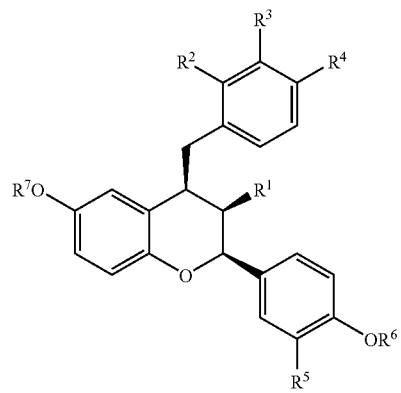

6a: $R^1$ = Et, $R^5$ = H, $R^6$ = $R^7$ = Butyryl, $R^2$ = $R^3$ = $R^4$ = H
6b: $R^1$ = Et, $R^5$ = H, $R^6$ = $R^7$ = Piv, $R^2$ = $R^3$ = $R^4$ = H
6c: $R^1$ = Et, $R^5$ = H, $R^6$ = $R^7$ = Me, $R^2$ = $R^3$ = $R^4$ = H Chroman 5b was dissolved in dry pyridine (5 ml/mmol). To this solution n-butyryl chloride or trimethylacetyl chloride (2.2-2.5 eq) was added dropwise. The reaction mixture was stirred for 2 hours at ambient temperature. The reaction mixture was taken up in ethyl acetate and washed with saturated sodium chloride solution and dried over anhydrous magnesiumsulphate. The solvent was evaporated and the crude product was purified by chromatography (toluene/diethyl ether) to give the products 6a and 6b, respectively, in 60-70% yield.

$R_f$=0.89 (toluene/diethyl ether 7:3).

Preparation of 6c 1.66 mmol of 5b was dissolved in 10 ml of dimethylformamide. 3.66 mmol (2.2 eq) of sodiumhydride (60% w/w in mineral oil) was added to the solution. 9.99 mmol (6 eq.) of methyl iodide was added dropwise to the solution while stirring. The reaction mixture was stirred for 2 hours at ambient temperature. The reaction mixture was poured into 20 ml of water. The product was extracted with 50 ml of dichloromethane. The organic layer was washed twice with 15 ml of water and dried over anhydrous magnesiumsulphate. The solvent was evaporated and the crude product was purified by column chromatography (toluene/ethyl acetate) to give product 6c in 53% yield.

$R_f$=0.92 (toluene/diethyl ether 7:3).

Example 6

The compounds of Examples 3 and 4, as well as sever other compounds (synthesized in unconventional manner) were tested for their estrogen receptor affinity, both as an agonist and as an antagonist.

Determination of competitive binding to cytoplasmic human estrogen receptor α or β from recombinant CHO cells is used to estimate the relative affinity (potency ratio) of a test compound for estrogen receptors present in the cytosol of recombinant Chinese hamster ovary (CHO) cells, stably transfected with the human estrogen receptor α (hERα) or β receptor (hERβ), as compared with estradiol ($E_2$).

The estrogenic and antiestrogenic activity of compounds is determined in an in vitro bioassay with recombinant Chinese hamster ovary (CHO) cells stably co-transfected with the human estrogen receptor α (hERα) or β receptor (hERβ), the rat oxytocin promoter (RO) and the luciferase reporter gene (LUC). The estrogenic activity (potency ratio) of a test compound to stimulate the transactivation of the enzyme luciferase mediated via the estrogen receptors hERα or hERβ is compared with the standard estrogen estradiol. The antiestrogenic activity (potency ratio) of a test compound to inhibit the transactivation of the enzyme luciferase mediated via the estrogen receptors hERα or hERβ by the estrogen estradiol is compared with the standard ICI 164.384 (=(7α,17β)-N-butyl-3,17-dihydroxy-N-methylestra-1,3,5(10)-triene-7-undecanamide).

| Compound | Potency Transactivation | β/α ratio |
| --- | --- | --- |
| 5a | ++ | +++ |
| 5b | +++ | +++ |
| 5c | ++ | +++ |
| 5d | + | +++ |
| 5e | +++ | +++ |
| 5f | ++ | +++ |
| 5g | ++ | +++ |
| 5h | + | ++ |
| 5i | + | ++ |
| 5j | +++ | +++ |
| 5k | ++ | +++ |
| 6a | +++ | +++ |
| 6b | + | + |

Potency(% relative to 17β-estradiol):
+ between 0.1-4%
++ between 4-10%
+++ >10%
β/α ratio:
+ between 3.5-10
++ between 10-30
+++ >30

The invention claimed is:

1. A chroman compound having formula 1

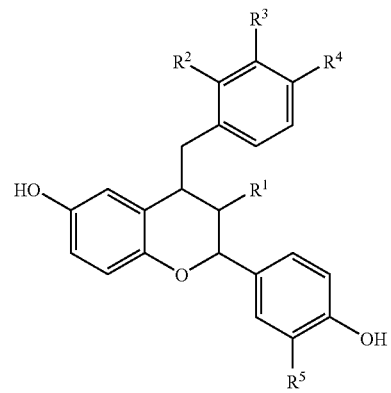

Formula 1 in which
$R^1$ is (1C-4C)alkyl, (2C-4C)alkenyl or (2C-4C)alkynyl, and independently $R^1$ has a cis-orientation in relation to the exocyclic phenyl group at the 2-position of the skeleton;
$R^4$ is Hal, $CF_3$, OH or (1C-2C)alkyloxy;
$R^2$, $R^3$, and $R^5$ are independently H, Hal, $CF_3$, (1C-4C) alkyl, (2C-4C)alkenyl, or (2C-4C)alkynyl;
or a prodrug thereof.

2. A pharmaceutical composition, comprising:
a pharmaceutically effective amount of the compound according to claim 1, and
pharmaceutically acceptable auxiliary.

3. A method of treating an estrogen-receptor related condition in a patient, comprising:
administering an effective amount of the compound according to claim 1,
wherein the estrogen-related condition is benign prostate hypertrophy, cardiovascular disorders, peri- and/or postmenopausal complaints, estrogen dependent tumor control, depression or Alzheimer's disease.

4. A chroman compound having formula 1

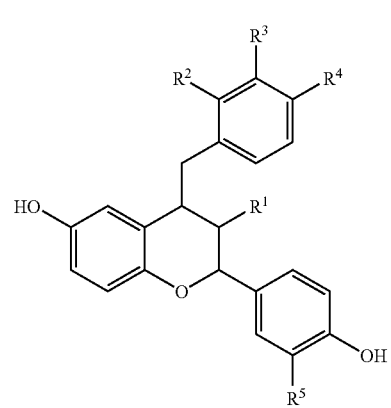

Formula 1 in which
$R^1$ is (1C-4C)alkyl, (2C-4C)alkenyl or (2C-4C)alkynyl, and independently $R^1$ has a cis-orientation in relation to the exocyclic phenyl group at the 2-position of the skeleton;
$R^4$ is H, Hal, $CF_3$, OH or (1C-2C)alkyloxy;
$R^2$, $R^3$, and $R^5$ are independently H, Hal, $CF_3$, (1C-4C) alkyl, (2C-4C)alkenyl or (2C-4C)alkynyl;
or a prodrug thereof.

5. A pharmaceutical composition, comprising:
a pharmaceutically effective amount of the compound according to claim 4, and
pharmaceutically acceptable auxiliary.

* * * * *